(12) United States Patent
Balmond

(10) Patent No.: US 10,012,582 B2
(45) Date of Patent: Jul. 3, 2018

(54) MASK FOR THE MANUFACTURE OF CORROSION SENSOR

(71) Applicant: BAE Systems plc, London (GB)

(72) Inventor: Mark David Balmond, Filton (GB)

(73) Assignee: BAE Systems plc, London (GB)

( * ) Notice: Subject to any disclaimer, the term of this patent is extended or adjusted under 35 U.S.C. 154(b) by 0 days.

(21) Appl. No.: 15/521,507

(22) PCT Filed: Feb. 4, 2015

(86) PCT No.: PCT/GB2015/050296
§ 371 (c)(1),
(2) Date: Apr. 24, 2017

(87) PCT Pub. No.: WO2016/075427
PCT Pub. Date: May 19, 2016

(65) Prior Publication Data
US 2017/0350808 A1      Dec. 7, 2017

(30) Foreign Application Priority Data
Nov. 14, 2014    (GB) .................................. 1420245.1

(51) Int. Cl.
*B32B 37/12*      (2006.01)
*B32B 38/00*      (2006.01)
*G01N 17/04*     (2006.01)

(52) U.S. Cl.
CPC .............. *G01N 17/04* (2013.01); *B32B 37/12* (2013.01); *B32B 38/0008* (2013.01); *B32B 2310/0806* (2013.01)

(58) Field of Classification Search
USPC ....... 156/230, 234, 240, 241, 247, 249, 250, 156/256, 267, 278
See application file for complete search history.

(56) References Cited

U.S. PATENT DOCUMENTS

| | | | |
|---|---|---|---|
| 4,837,049 A | * | 6/1989 | Byers ................... A61B 5/0422 216/11 |
| 5,120,572 A | * | 6/1992 | Kumar ..................... H05K 1/16 148/DIG. 136 |

(Continued)

FOREIGN PATENT DOCUMENTS

| | | |
|---|---|---|
| DE | 202014101068 U1 | 5/2014 |
| EP | 2306175 A1 | 4/2011 |

(Continued)

OTHER PUBLICATIONS

International Preliminary Report on Patentability of International Application No. PCT/GB2015/050296, dated May 17, 2016, 11 pages.

(Continued)

*Primary Examiner* — Sing P Chan
(74) *Attorney, Agent, or Firm* — Maine Cernota & Rardin

(57) ABSTRACT

A method of manufacturing a sensor (1), such as a corrosion sensor, a mask including a series of masking elements (21, 22, 23) for masking a corresponding series of sensing elements (12, 13, 14), a sensing element having such a mask and a sensor are provided. The sensor (1) includes a number of metallic strips (12, 13, 14) mounted on a non-conducting substrate (9) and a module (3) for forming electrical connections to the strips whereby to enable communication between the strips (12, 13, 14) and monitoring equipment for the sensor (1). The module includes a number of wire connections (15, 16, 17, 18) and the method includes the steps of encapsulating the wire connections within a flexible chemical and heat resistant sealing compound and subsequently encapsulating the flexible sealing compound within a second sealing compound by an injection molding process. The sensing elements (12, 13, 14) are covered by the masking elements (21, 22, 23) prior painting the sensor (1) with a corrosion-inhibiting paint. The masking elements (21, (Continued)

22, 23) are made of a material allowing only weak adherence of paint in order to have sharp paint edges around the sensing elements (12, 13, 14). Sharp edges allow the corrosion-inhibiting agents to leach onto the sensing elements (12, 13, 14).

11 Claims, 5 Drawing Sheets

(56) References Cited

U.S. PATENT DOCUMENTS

| | | | | |
|---|---|---|---|---|
| 5,191,708 A * | 3/1993 | Kasukabe | ........ | G01R 1/06711 216/11 |
| 5,200,362 A * | 4/1993 | Lin | ........ | H01L 21/56 257/E21.502 |
| 5,254,493 A * | 10/1993 | Kumar | ........ | H05K 1/16 148/DIG. 136 |
| 5,994,156 A * | 11/1999 | Voutsas | ........ | H01L 21/02071 257/E21.19 |
| 6,010,966 A * | 1/2000 | Ionov | ........ | H01L 21/32136 252/79.1 |
| 6,080,529 A * | 6/2000 | Ye | ........ | H01L 21/0274 430/318 |
| 6,331,380 B1 * | 12/2001 | Ye | ........ | H01L 21/0274 257/E21.027 |
| 6,383,720 B1 * | 5/2002 | Nakashima | ........ | H05K 3/205 430/313 |
| 6,631,022 B1 * | 10/2003 | Kihira | ........ | G02F 1/1506 348/E5.028 |
| 7,049,235 B2 * | 5/2006 | Park | ........ | G03F 7/423 430/331 |
| 9,921,697 B2 * | 3/2018 | Lee | ........ | G06F 3/044 |
| 2001/0041453 A1 * | 11/2001 | Ohuchi | ........ | C23F 4/00 438/712 |
| 2003/0026959 A1 * | 2/2003 | Furuse | ........ | G03F 7/405 428/195.1 |
| 2003/0029232 A1 * | 2/2003 | Felix | ........ | G01N 17/043 73/86 |
| 2006/0267120 A1 * | 11/2006 | Nakahori | ........ | G02F 1/133555 257/414 |
| 2008/0002077 A1 * | 1/2008 | Kim | ........ | G02F 1/13454 349/42 |
| 2008/0030668 A1 * | 2/2008 | Komaju | ........ | G02F 1/1345 349/151 |
| 2009/0290083 A1 * | 11/2009 | Lim | ........ | G02F 1/1368 349/46 |
| 2013/0001563 A1 * | 1/2013 | Park | ........ | H01L 27/3276 257/59 |
| 2013/0015457 A1 * | 1/2013 | You | ........ | H01L 27/1288 257/71 |
| 2013/0227835 A1 * | 9/2013 | Chiba | ........ | G01R 1/067 29/592.1 |
| 2013/0320322 A1 * | 12/2013 | Muto | ........ | H01L 51/0021 257/40 |
| 2014/0014400 A1 * | 1/2014 | Mori | ........ | B29C 45/1418 174/254 |
| 2016/0162062 A1 * | 6/2016 | Furukawa | ........ | G06F 3/041 345/173 |
| 2016/0320872 A1 * | 11/2016 | Lee | ........ | G06F 3/044 |
| 2017/0363486 A1 * | 12/2017 | Okulov | ........ | G01L 1/005 |

FOREIGN PATENT DOCUMENTS

| | | |
|---|---|---|
| GB | 2505069 A | 2/2014 |
| WO | 2008125878 A1 | 10/2008 |
| WO | 2009141639 A1 | 11/2009 |
| WO | 2010126429 A1 | 11/2010 |

OTHER PUBLICATIONS

Great Britain Search Report of Appl No. GB1420245.1, dated Apr. 14, 2015, 4 pages.
International Search Report and Written Opinion of Appl No. PCT/GB2015/050296, dated Jun. 26, 2015, 17 pages.

* cited by examiner

MASK FOR THE MANUFACTURE OF CORROSION SENSOR

RELATED APPLICATIONS

This application is a National Phase application filed under 35 USC § 371 of PCT Application No. PCT/GB2015/050296 with an International filing date of Feb. 4, 2015, which claims priority of GB Patent Application GB1420245.1 filed Nov. 14, 2014. Each of these applications is herein incorporated by reference in its entirety for all purposes.

FIELD OF THE INVENTION

This invention relates to the manufacture of sensors which may be used for detecting corrosion on a metallic material, paint defects or degradation, etc.

BACKGROUND

Such sensors, especially corrosion sensors, are extremely thin and small (of the order of 2 cm square) and are often placed in inaccessible or difficult to access locations on structures such as drill rigs or vehicles such as aircraft, ships or land vehicles. Corrosion of metallic structures, particularly in corrosive environments such as on seagoing vessels or carrier-based aircraft, is an enormous financial problem for operators and can amount to billions of dollars per annum, as is the case, for example, for the US military. Thus the use of such sensors as corrosion sensors, which can be used to signal various stages of corrosion of a structure on which they are mounted, can give the owner remote information on the state of corrosion of areas which are hard-to-access, are functionally critical or are highly numerous and would otherwise lead to excessive inspection time. Corrosion of the sensor may also be used as an indication of paint degradation or of defects occurring in a layer of paint.

Sensors of this type are both difficult and expensive to manufacture, being fabricated in clean rooms, using silicon chip manufacturing technology.

SUMMARY

Looking now at the construction of the sensor, the sensor consists of a sensor chip or "sensing element" coupled with a connecting module containing electrical connections between the chip and external monitoring means. The chip may consist of a thin substrate, for example silicon, which may be coated with an insulator such as silicon dioxide. The substrate may be flexible and may also be of a material such as polyimide which may act as both substrate and insulator. Onto the insulator is deposited at least one layer of conducting material, such as aluminium alloy, which may be formed, using masking technology, into a single strip or into strips of different width. The thickness of the layer forming the strip or strips may be approximately 150 nm.

The aforementioned circuitry is designed to communicate signals from the strip or strips as they corrode, to remote monitoring equipment. Normally, the increase in strip resistance is measured, as its cross sectional area decreases with corrosion.

The conducting strip or strips and connecting tracks are integrally formed on the substrate from a conducting material designed to be the same as or to mimic the corrodible material on which the sensor is to be mounted in use. An example of this conducting material would be aluminium alloy for use on aircraft. The chip is then painted. This paint may be the same paint as will be used to cover the corrodible material on which the sensor is to be mounted. For ships and aircraft, the paint would be a paint containing a corrosion inhibitor and, although not essential, such chips are primarily designed to be used with paints containing a corrosion inhibitor.

For aircraft applications, the paint is generally applied all over the sensor chip save for the conducting strip, or strips, which are left bare. The relatively narrow width of the exposed strips, eg., from 0.2 mm to 4 mm, is designed to represent paint flaws or other damage which may occur to the paintwork such as cracks, scratches, chips etc. If corrosion inhibitor paint is used, the inhibitor will leach out from the paint and spread over the bare strips. Depending upon the width of the strip, the leaching inhibitor will either fully or partially protect the strip from corrosion. For wider strips, only partly protected, corrosion will attack almost immediately. For narrower strips, protection will last longer. In this way, the sensor will provide sensing with different sensitivities and with different lifetimes, depending upon strip widths.

Manufacture of such sensors to the required accuracy is extremely difficult. In order to position the gaps, representing flaws in the paint, with sufficient accuracy over the conducting tracks, it is necessary to position paint masking elements to an accuracy of approximately 50 microns. Economical manufacturing of sufficient numbers of sensors at a time requires large numbers of masking elements, say approximately fifty at a time, to be accurately positioned on the chip. With currently known methods this has been next to impossible.

Initially, the application of a thick photoresist layer, to act as a paint mask, was tried using spin coating and laminating techniques. This was not successful. After this, deposition of other materials and patterning with photoresist in order to form a paint mask was attempted, again without success. All of these layers, however thick, were buried under the tough paint. To use this method would require accurate machining off of paint until the mask elements were reached. This would have been a extremely time-consuming process and thus impractical. An additional problem was that removal of the masking elements, once exposed, was an overnight process of chemical removal. This process also risked damage to the remaining paint and additionally often required additional brushing which tended to damage the surface of the conductive tracks.

Even masking which was thicker than the paint was unsuitable. Adhesion of edges of the mask to the paint caused uncertain edge definition, for the paint, and thus the required positional accuracy of the gaps in the paint, representing the flaws, could not be achieved.

The above methods of applying a mask were tried in an effort to have a process which would allow bulk positioning and removal of masking elements, as so many needed to be positioned and removed each time.

However, as the above methods were not practical, an alternative method of masking the chip had to be found. The masking material chosen had to repel the paint, otherwise the required accuracy of edge definition, around edges of the masking elements, could not be achieved. PTFE was then found to have the required paint repelling properties. This was only available in blocks, however, which were costly to machine to the required shape of each element and were difficult to fix on the chip without leaving adhesive residue. In addition, in order to be handled, the individual masking elements would need to be approximately 2 mm thick which was far thicker than ideally required. Furthermore, the requirement to locate up to fifty such elements on each multi-chip substrate to an accuracy of 50 microns would mean that it would not be a simple task to locate the masking elements on each multi-chip substrate to be painted. Furthermore, manufacturing of such small components is relatively expensive in comparison with the cost of the sensor chip production.

According to a first aspect of the present invention there is provided a method of applying a series of masking elements to a sensing element, the sensing element comprising a layer of conducting tracks applied to a non-conducting substrate and the series of masking elements being accurately applied to the conducting tracks, the method including the steps of mounting a sheet of masking material on a backing layer, accurately cutting out the series of masking elements on the backing layer, removing unwanted masking material from the backing layer, mounting a said backing layer with the masking elements thereon to a mount of positional fine adjustment means, said mount being finely adjustable with respect to the sensor along three mutually orthogonal axes, positioning the backing layer such that the series of masking elements lie in non-contacting face-to-face relationship with the conducting tracks and such that a magnifying optical viewer for a user is capable of keeping the conducting tracks and the masking elements substantially in focus simultaneously, fine adjusting the mount with respect to the sensor whereby accurately to position the masking elements with respect to parts of the conducting tracks to be masked thereby, moving the mount and the masking elements together to bring the masking elements into contact with the conducting tracks, demounting the backing layer from the mount, and peeling the backing layer from the masking elements.

The sheet of masking material may be mounted to a transparent said backing layer being at least partially transparent to electromagnetic radiation used to operate the optical viewer whereby to allow the user to view the sensor and the sheet of masking material through the transparent backing layer. Application tape, which has no significant stretch, as used in this application, was found to be suitable as a transparent backing layer. In addition, the transparent backing layer needed an appropriate level of tack to allow the transparent backing layer to be peeled from the masking elements, once they are in position on the sensing element, without removing the masking elements from the sensing element.

The sheet of masking material may be mounted on a non transparent backing layer for the cutting out of the series of masking elements and thereafter the masking elements may be mounted on a transparent said backing layer at least partially transparent to electromagnetic (EM) radiation used to operate the optical viewer prior to mounting the masking elements to the mount.

The masking elements may be mounted on the transparent backing layer by providing a tacky front surface on the transparent backing layer and applying the tacky surface to the masking elements, applying a transparent temporary adhesive to a rear surface of the transparent backing layer, mounting the transparent backing layer to the mount and removing the non transparent backing layer from the masking elements.

The mount may include a rigid sheet of material transparent to the said EM radiation and in which the transparent backing layer may be mounted to the rigid sheet by the temporary adhesive. The rigid sheet is desirably flat in order to allow the whole series of masking elements to be substantially in focus simultaneously with the conductive tracks.

The rigid sheet of transparent material may be attachable to the remainder of the positional fine adjustment means by a vacuum chuck in which a vacuum is applied to an edge region of the rigid sheet of transparent material in order to hold it in position on the positional fine adjustment means.

The substrate may be formed at least partially transparent to electromagnetic radiation used to operate the optical viewer whereby to allow the user to view the sheet of masking material through the substrate.

Fine adjusting the mount with respect to the sensor whereby accurately to position the masking elements with respect to parts of the conducting tracks to be masked thereby may include the step of aligning chosen respective correspondence points on the backing layer for the masking elements and conducting tracks or sensing element. In this way, say, two sets of correspondence points may be aligned which will ensure full alignment of the tracks with the masking elements.

The sets of correspondence points will desirably be positioned in peripheral positions and preferably on opposite sides of the sensing element whereby to ensure that no alignment errors are greater than those which may occur between the sets of correspondence points.

The backing layer may be demounted from the mount by a peeling step.

The sheet of masking material provided should comprise a material having a surface property adapted to allow only weak adherence of paint thereto. The releasable mask may comprise a substrate with a first chemically resistant surface, and a second surface having a release layer. The release layer may be provided by a releasable adhesive coating, such as for example a pressure sensitive adhesive or a hot melt adhesive.

The releasable mask substrate may be rigid or, more preferably, flexible to allow the mask to readily adapt to the shape of the element to be masked. The mask substrate may be manufactured from a flexible polymer, rubber or metal film. The flexible polymer may be any suitable polymer, co-polymer or block polymer, for example, halogenated polymers, polyamides, such as (Kapton®), polyesters, polyurethanes or laminated substrates which has the required weak paint adherence properties. Halogenated polymers, for example, PVC, PTFE, provide good die-cutting properties, such as to allow clear edge definition of the cut mask material at the micron level. Further, halogenated polymers provide good chemical resistance to solvents, detergents, acids, alkalis and paint formulations.

Mask thickness as a practical matter is dictated by two factors. Firstly, it is desirable for the mask to be at least as thick as the paint. Secondly, it is necessary to be able to accurately position the mask and fix it in position with temporary adhesive. Thus, for a normal thickness of, say, 50 microns of aircraft quality paint to be applied to the sensor, the mask may have a thickness in the range of 50 to 250 microns, preferably in the range of 75 to 150 microns.

According to a second aspect of the invention there is provided a method of manufacturing a sensing element including carrying out the method of the first aspect of the invention and thereafter carrying out the steps of coating the sensing element having the series of masking elements applied thereto with a layer of corrosion-resistant material and thereafter removing the series of masking elements whereby to expose selected areas of the conducting tracks to corrosive influence.

The method may include the step of connecting the conducting tracks to a connection module adapted to allow connection of the conducting tracks of the sensor to monitoring means.

According to a third aspect of the invention there is provided a mask for masking a series of sensing elements in which each sensing element has a series of conductive tracks deposited on a non conducting substrate, the mask comprising a series of masking elements to cover each sensing element, wherein the mask comprises a material having a surface property adapted to allow only weak adherence of paint thereto, such as high surface energy.

According to a fourth aspect of the invention there is provided a sensing element having a mask according to the third aspect applied thereto.

According to a fifth aspect of the invention there is provided a sensing element manufactured according to the method of the second aspect of the invention.

According to a sixth aspect of the invention there is provided a sensor comprising a sensing element according to the fifth aspect of the invention joined to a connecting module adapted to connect the sensor to monitoring means, the sensing element being manufactured according to the method of the second aspect of the invention.

BRIEF DESCRIPTION OF THE FIGURES

The invention will now be further described by way of example, only, with reference to the accompanying drawings of which.

DETAILED DESCRIPTION

Figure 1:
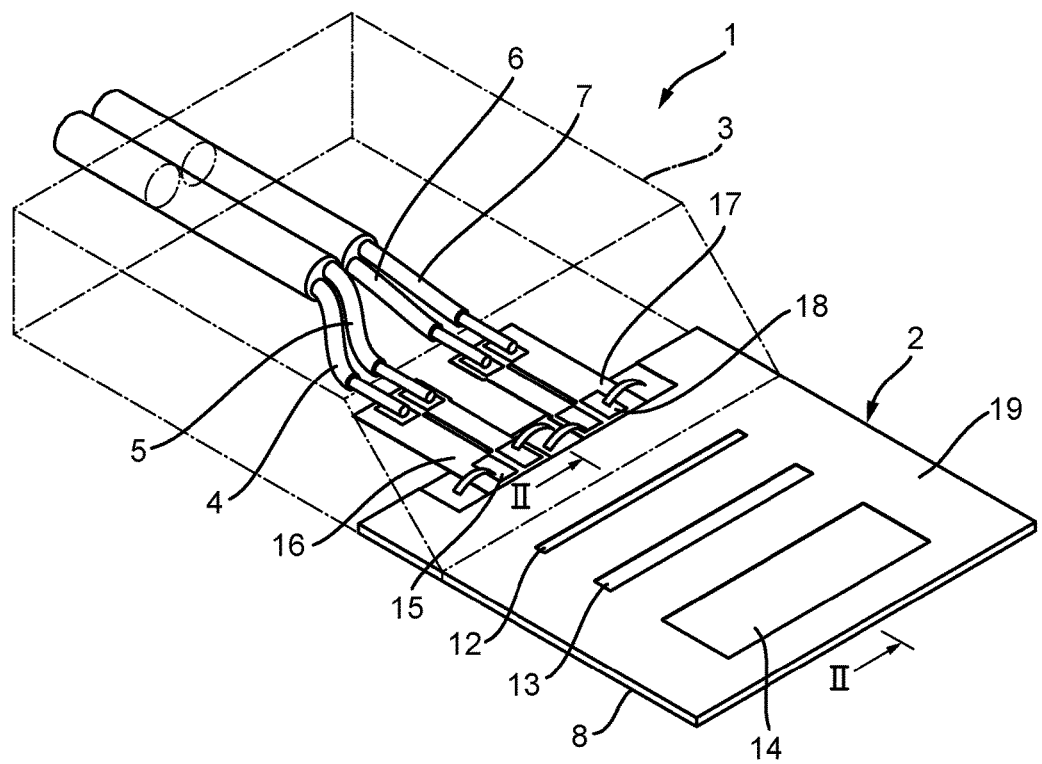
FIG. 1 is a ghosted three dimensional sketch of a corrosion sensor made according to the invention.

Referring to FIG. 1, a sensor 1 made according to the invention is shown. The sensor 1 comprises a corrosion sensing element 2 and a connecting module 3, adapted to allow connection of the corrosion sensor via wires 4, 5, 6 and 7 to separate corrosion monitoring means (not shown). Four wires 4 to 7 are shown connecting to the connecting module 3, rather than just two, owing to the use of a Wheatstone Bridge arrangement (not shown) for interpreting the results. Both the corrosion sensing element 2 and the module 3 are formed on a single rigid substrate 9 of silicon.

Figure 2:
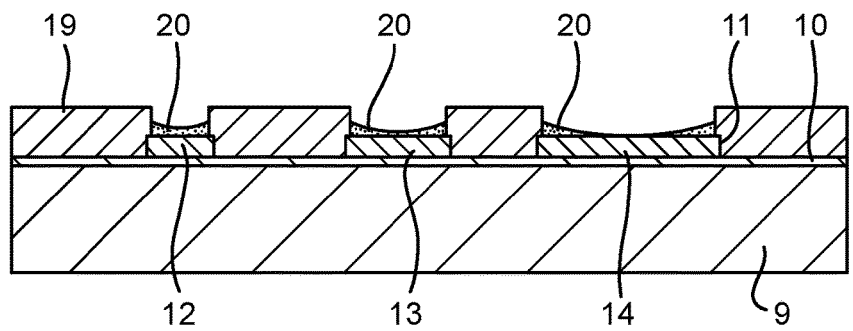
FIG. 2 is a schematic sectional view II-II of a corrosion sensing element of the sensor of FIG. 1.

Referring initially to the corrosion sensing element 2, as shown in FIG. 2, this consists of the substrate 9 of silicon on which is formed a thin layer 10 of silicon dioxide which acts as an insulator. Onto the layer of silicon dioxide 10 is deposited a double layer 11 of aluminium alloy material. This double layer 11 also appears in the drawing as strips 12, 13 and 14 and strip pads 15, 16, 17 and 18. Over the double layer 11 of aluminium alloy is applied at least one layer 19 of paint which has gaps corresponding to the strips 12, 13 and 14 and the strip pads 15 to 18.

The paint 19 and the aluminium alloy 11 will be selected to correspond as closely as practicable to those in use of a metallic painted material whose corrosion is to be monitored by the corrosion sensor. Where the paint 19 contains corrosion inhibitor 20, as shown, this will leach out of the paint over the otherwise unprotected strips 12, 13 and 14. That part of the strip 12, 13, 14 covered by the inhibitor will be protected from corrosion. If the inhibitor fails to reach right across the strip, however, such as for the widest strip 14, then corrosion of that strip will set in as soon as it becomes subject to corrosive influence. In a similar manner, once corrosion inhibitor has ceased to leach out of the paint onto the remaining strips 12, 13, the strips will be left unprotected and corrosion will begin. With the strips shown, widest strip 14 will begin to corrode first, followed by the centre strip 13 and finally by the narrowest strip 12. The sensor thus enables measurement of corrosion at different sensitivities and over differing periods, using the sensor strips 12, 13, 14 of differing widths.

Strip pads 12 to 15 are connected, under the paint, to strips 12, 13 and 14 such that the voltage or current from each strip can be measured separately.

Figure 3:
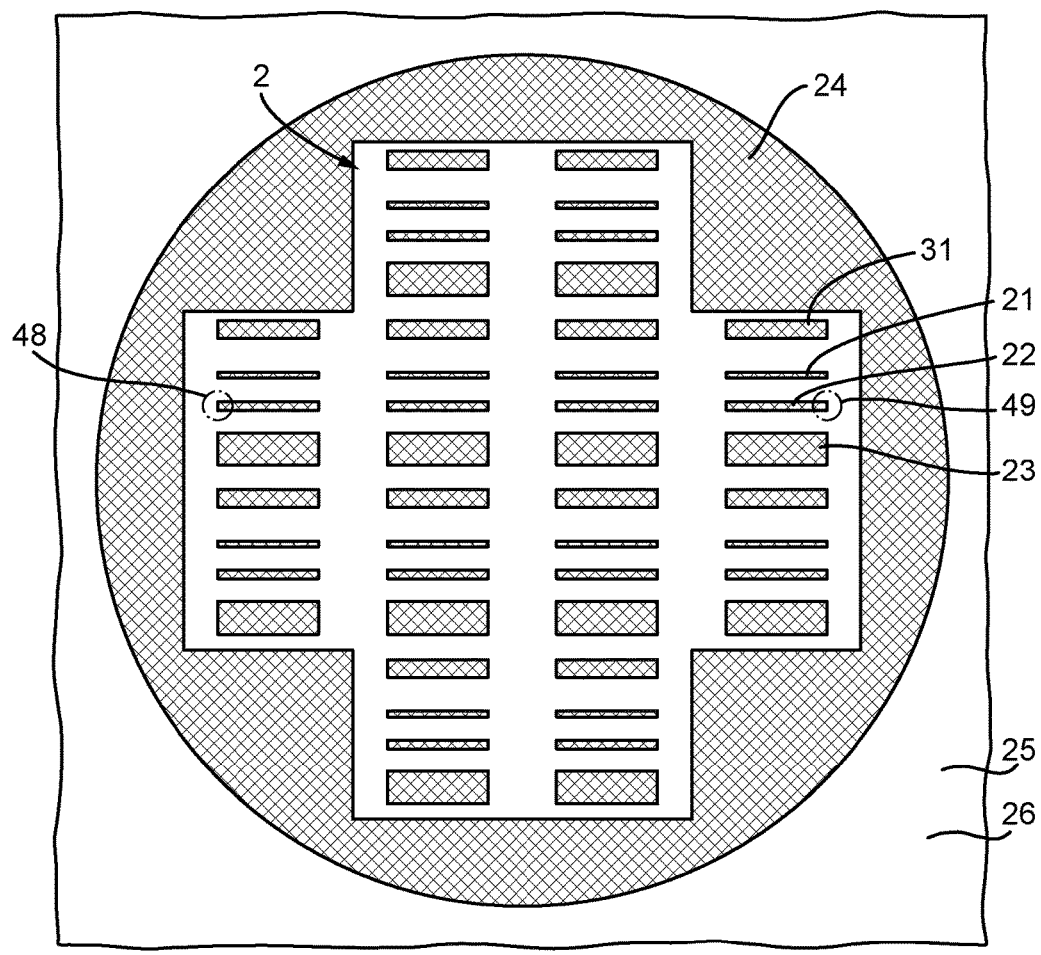
FIG. 3 is a schematic plan view of a series of masking elements on a backing layer.

FIG. 3 shows a series of masking elements 21, 22, 23 cut out from a sheet 24 of masking material. Masking elements 21, 22, 23, for use in masking twelve corrosion sensing elements 2 are shown. The sheet of masking material is applied to a backing layer 25 and is viewed through a transparent second backing layer in the form of a transfer film 26. The backing layers 25, 26 are thus applied to opposite sides of the sheet of masking material 24. Unwanted masking material has been peeled from the backing layer 25 and is not shown.

The masking material used is a high surface energy, translucent calendered matt PVC material 100 microns thick, known as "Paintmask Blue" and manufactured by Victory Design Limited, 41 Creswell Road, Clowne, Chesterfield, Derbyshire. Paintmask Blue is supplied on a PE coated silicone release paper and with a peelable acrylic adhesive of medium tack. It is designed for use between −20 deg.C. and +70 deg.C. The product is easily cuttable and, as particularly required by this invention, has an extremely clear edge definition. It is sold for use in paint masking, for the sides of commercial vehicles.

Figure 4:
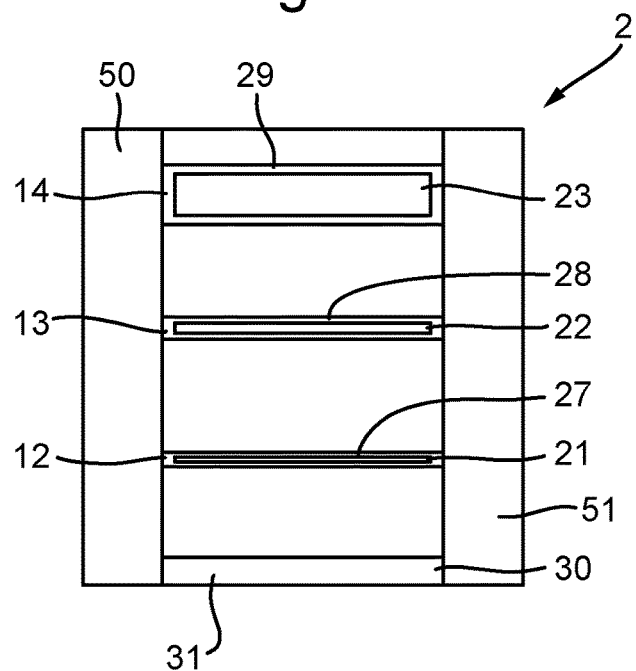
FIG. 4 is a schematic plan view of an unpainted corrosion sensing element having masking elements according to the invention positioned thereon.

As shown in FIG. 4, each corrosion sensing element 2 requires three masking elements 21, 22, 23 to cover the three strips 12, 13, 14 of conductive material. The three strips 12, 13, 14 join together two bus bars 50, 51 to which the wire connections will be directly or indirectly made. It will be observed that each masking element 21, 22, 23 is accurately positioned on each conductive strip 12, 13, 14 so as to leave a border region 27, 28, 29 of exposed strip of precisely defined dimensions. The method of the present invention is directed to accurately achieving the selected dimensions of these border regions by the accurate placement of the masking elements 21, 22, 23 on the conductive tracks 12, 13, 14. For corrosion sensors of the type described here, with the corrosion sensing element being approximately 2 cm square, the masking elements 21, 22, 23 must be positioned to an accuracy of approximately 50 microns.

An area 30 on the sensing element 2 has also been covered by a masking element 31. This area is where the strip pads 15, 16, 17 and 18 are to be located and also needs to be free of paint.

Figure 5:
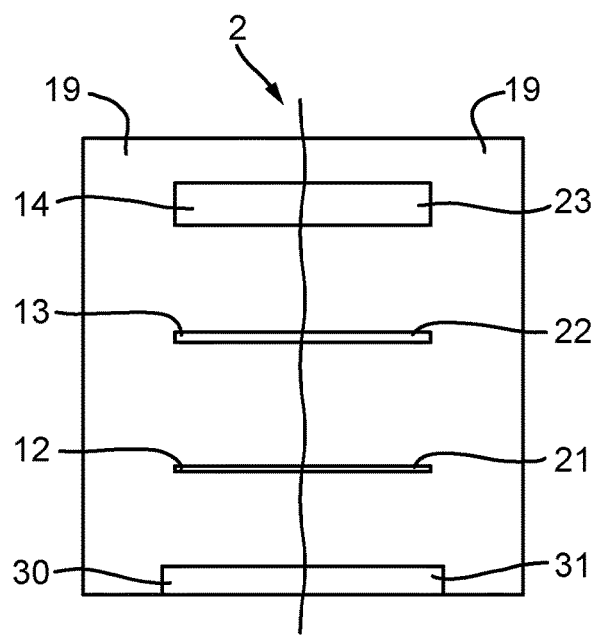
FIG. 5 is a plan view of the corrosion sensing element of FIG. 4, the left hand side shown painted with masking elements removed and the right hand side shown painted but with the masking elements still in place, prior to removal.

FIG. 5 shows a split view of a corrosion sensing element 2. On the left hand side is shown an element 2, paint 19 having been applied thereto and masking elements removed. Masking elements 21, 22, 23 and 31 were used to protect conductive strips 12, 13, 14 and area 30, during painting, and thereafter were removed to leave the strips exposed.

In the right side view, the sensing element 2 has also been painted but the masking elements 21, 22, 23 and 31 are still in position, covering the conductive strips 12, 13, 14 and the strip pad area 30.

Figure 6:
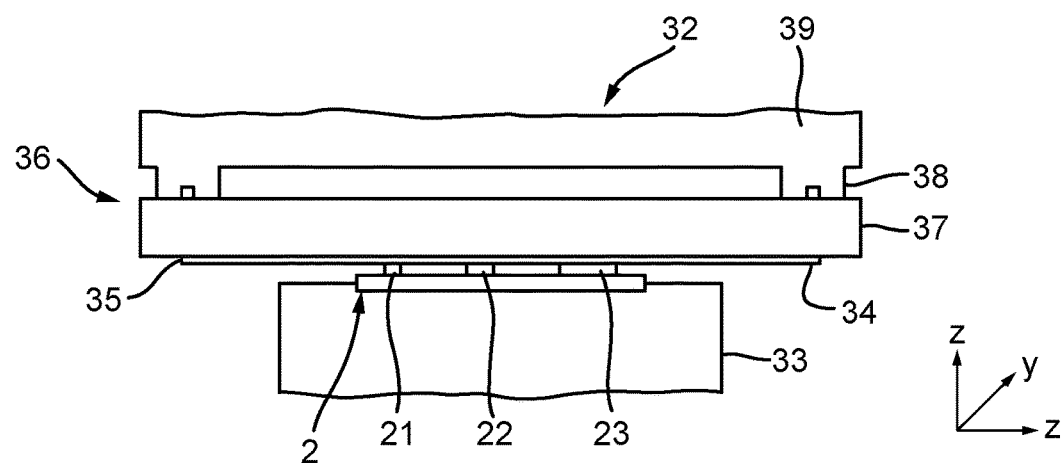
FIG. 6 is a schematic side view of positional fine adjustment means holding a series of masking elements on a backing layer and of a corrosion sensing element.

FIG. 6, shows positional fine adjustment means 32 holding a series of masking elements 21, 22, 23 for one sensing element 2. The masking elements 21, 22, 23 are attached to a transparent backing layer in the form of a transfer film 34 and are shown having been moved into contact with a corrosion sensing element 2 held in a support 33 of the positional fine adjustment means 32. The transfer film 34, to which the masking elements 21, 22, 23 are attached is attached by spray-mount transparent temporary adhesive 35 to a mount 36 of the positional fine adjustment means 32. The mount 36 comprises a flat slab of glass 37 attached by a vacuum chuck 38 to a movable table 39. The movable table 39 is finely adjustable by a user in three mutually orthogonal directions, X, Y and Z, as shown.

It will be appreciated that FIG. 1 shows a series of masking elements for 12 sensing elements 2, rather than the one set shown for illustration purposes in FIG. 6. In practice, for reasons of economy of manufacture, a number of sensing elements 2, corresponding to the number of sets of masking elements on a sheet 24, would be combined on a single substrate and suitably held in the support 33. Here, a circular non-conducting substrate such as an oxidised silicon wafer or FR4, having a diameter corresponding to that of the sheet 24 of masking material, would have one or two layers of conducting metal alloy deposited on the substrate and etched away in a known manner to leave the required configuration of conductive strips or tracks on the substrate. In this way, the full potential advantage of the invention may be taken and, as here, 48 individual conductive strips 12, 13, 14, and strip pad areas 30 may be masked by masking elements 21, 22, 23 and 31 at one time and with the required degree of accuracy.

Figure 7:
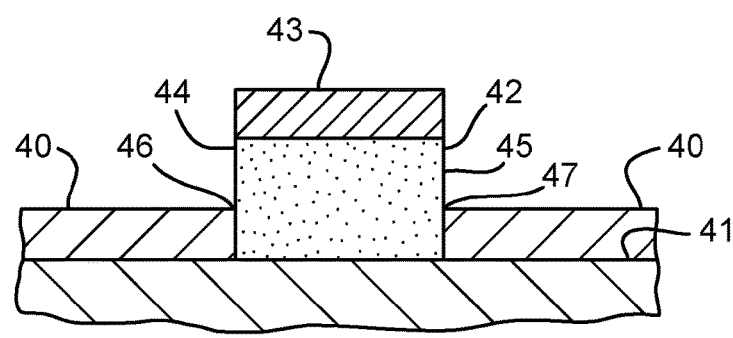
FIG. 7 is a schematic side sectional view of a detail of paint applied to a metal track masked by a masking element.

FIG. 7 is a schematic side sectional detail view of paint 40, 43 applied to a metal track 41 over a masking element 42. The drawing is not to scale and shows what happens if a block of Paintmask Blue masking material 42, thicker than the paint 40, is individually placed on the metal track 41 and paint 40 is applied. It can be seen that the paint will not adhere to sides 44, 45 of the block 42 of masking material and will thus allow very clean edge definition of the paint 40, 40 where it meets the masking material 42 at edges 46, 47 of the paint.

Figure 8:
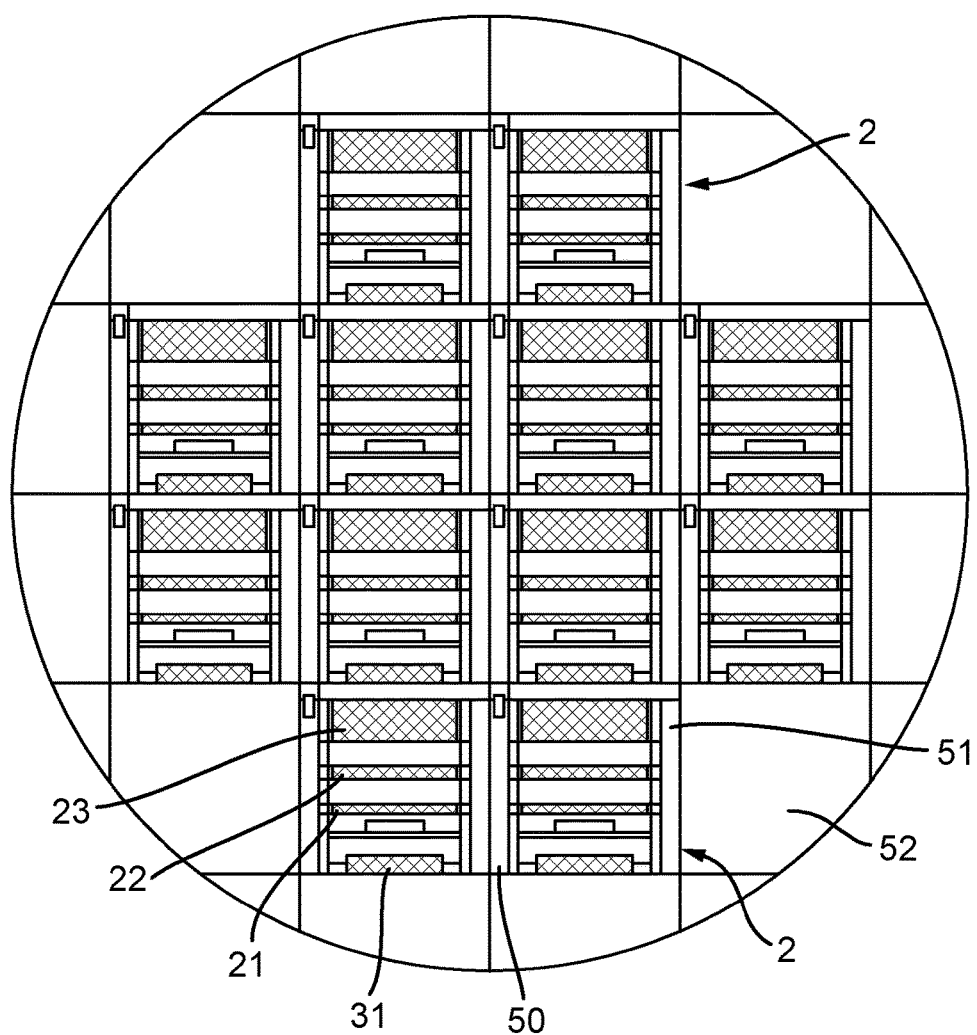
FIG. 8 is a schematic top plan view of a circular substrate containing twelve corrosion sensing elements.

FIG. 8 shows a circular substrate 52 containing twelve corrosion sensing elements 2. The substrate 52 has a series of forty eight masking elements 21, 22, 23, 31 applied to it as follows.

Firstly, a sheet 24 of masking material, here Paintmask Blue, mounted on a waxed paper backing layer 25 is accurately cut, whereby to cut out a series of forty eight masking elements 21, 22, 23, 31. Currently a plotter is used for this task. However, a laser cutter could equally be used and this tool may be more suitable for cutting out smaller masking elements. Next, unwanted masking material is peeled off to leave the pattern shown in FIG. 3. Then, a transparent second backing layer in the form of application tape 26 is rolled onto the masking material shown in FIG. 3. Thus, the masking material has the original paper backing layer 25 on one side and the application tape 26 on the other. The paper backing layer 25 is then peeled off, leaving the masking elements on the application tape 26.

As an alternative to cutting out the masking elements while on the waxed paper backing layer 25 and then transferring the masking elements to the transparent application tape, it may be convenient initially to mount the sheet of masking material 24 on some form of transparent backing layer and to cut out the masking elements on this transparent layer. A material similar to application tape may be used which is usually formed from polythene. In addition, acetate sheet or glass may be used. With glass, a temporary adhesive to allow attachment of the mask may be used. If glass is used, laser cutting of the paint masks may be employed and, indeed, laser cutting may be substituted for plotter cutting, whatever the backing layer.

In order to position all the masking elements with respect to the sensing element 2 to the required accuracy of 50 microns, it was necessary to consider the use of a microscope. However, with the masking elements simply mounted on the flexible application tape 26, it would be difficult to support the masking elements such that they were all in a one focal plane, while having their position adjusted with respect to the sensing element.

In order to try and solve this problem, the following method was adopted. Spray mount temporary adhesive 35 was sprayed onto a rear surface of the application tape 26 and the application tape 26 was pressed onto a flat slab of glass 37 and rolled, to achieve good adhesion and to ensure that the masking elements 21, 22, 23, 31 are held flat on the glass.

After this, the slab of glass, with the exposed masking elements directed downwardly was attached to the movable table 39 of the positional fine adjustment means 32 by the vacuum chuck 38. By this method, it was possible to support all the masking elements in a single plane, which would facilitate use of a microscope when making positional adjustments.

Next, the corrosion sensing element 2 is mounted on the support 33 of the positional fine adjustment means 32, ready to receive the masking elements 21, 22, 23, 31, once they have been accurately positioned with respect to the conductive tracks 12, 13, 14 and strip pad areas 30 of the sensing element 2.

Next, the movable table 39 is lowered along the Z axis until the masking elements are separated from the sensing element 2 by approximately 1 mm. The reason for this is to position the masking elements and the sensing element as nearly as possible in one focal plane, as has been explained above, for viewing both simultaneously with a microscope.

With the separation set at 1 mm, coarse adjustment of the movable table 39 with respect to the sensing element 2, in the X and Y axes, is carried out. In order to facilitate this adjustment, and to avoid having to inspect and adjust the separation of a large number of features on the application tape 26 and the sensing element 2, respectively, two sets of correspondence points on the application tape 26 and sensing element 2 are chosen and marked. These are located on opposite sides of the sensing element 2 to ensure that any positional errors remaining, once adjustment is made, cannot exceed that at the correspondence points. If desired, two viewing windows (not shown) may be arranged, in the glass for example, such that the user of the positional fine adjust means 32 can only see the sensing element through these windows. Thus, when respective correspondence points 48, 49 on the application tape 26 and sensing element 2 match up, all masking elements will align with their respective conductive tracks.

Next, the table 39 is further wound down to a separation between the application tape 26 and sensing element 2 of approximately 100 microns and any further necessary positional adjustments are made. Such errors can occur, owing to inaccuracies within the mechanism of the positional fine adjustment means 32.

Next, the table 39 is wound down to bring the masking elements and the sensing element 2 into contact. At this point, vacuum is released from the vacuum chuck 38 and the glass slab 37, with the masking elements and sensing element 2 attached, is lifted from the support 33. The application tape is released from the glass by a rapid peeling of the tape 26 from the glass 37. It will be appreciated that for the above separation properly to take place, it is necessary for the tack level between the sensing element and masking elements to be arranged to be stronger than between the masking elements and the application tape.

The sensing element 2 is thus ready for application of paint. This may take place before or after the corrosion sensor is located in position, for corrosion detection. This is usually done at the corrosion sensor manufacturing stage, however.

Once the sensing element is painted, the masking elements are removed by chemical means. The removal chemical seeps under each masking element via the edges thereof, where the masking element meets the paint, to lift off the element. Currently, alcohol is used as certain chemicals may risk damaging the paint. This is a relatively speedy process, taking only a few minutes.

The sensing element may be painted before its separation into its respective individual sensor chips or after. This is currently done before.

Next, the connecting wires 4, 5, 6, 7 are soldered to the strip pads 15, 16, 17, 18 and the connecting module casing 3 is injection moulded around the sensing element and wires.

What is claimed is:

1. A method of applying a series of masking elements to a sensing element, the sensing element comprising a layer of conducting tracks applied to a non-conducting substrate and the series of masking elements being accurately applied to the conducting tracks, the method including the steps of:
   mounting a sheet of masking material on a backing layer;
   accurately cutting out the series of masking elements on the backing layer;
   removing unwanted masking material from the backing layer;
   mounting said backing layer with the masking elements thereon to a mount of positional fine adjustment means, said mount being finely adjustable with respect to the sensor along three mutually orthogonal axes;
   positioning the backing layer such that the series of masking elements lie in non-contacting face-to-face relationship with the conducting tracks and such that a magnifying optical viewer for a user is capable of keeping the conducting tracks and the masking elements substantially in focus simultaneously;
   fine adjusting the mount with respect to the sensing element whereby accurately to position the masking elements with respect to parts of the conducting tracks to be masked thereby;
   moving the mount and the masking elements together to bring the masking elements into contact with the conducting tracks;
   demounting the backing layer from the mount; and
   peeling the backing layer from the masking elements.

2. A method as in claim 1, in which the sheet of masking material is mounted to a transparent backing layer being at least partially transparent to electromagnetic radiation used to operate the optical viewer whereby to allow the user to view the sensing element and the sheet of masking material through the transparent backing layer.

3. A method as in claim 1, in which the sheet of masking material is mounted on a non-transparent backing layer for the cutting out of the series of masking elements and thereafter the masking elements are mounted on a transparent backing layer at least partially transparent to electromagnetic (EM) radiation used to operate the optical viewer prior to mounting the masking elements to the mount.

4. A method as in claim 3, in which the masking elements are mounted on the transparent backing layer by providing a tacky front surface on the transparent backing layer and applying the tacky surface to the masking elements, applying a transparent temporary adhesive to a rear surface of the transparent backing layer, mounting the transparent backing layer to the mount and removing the non-transparent backing layer from the masking elements.

5. A method as in claim 4, in which the mount includes a rigid sheet of material transparent to the said EM radiation and in which the transparent backing layer is mounted to the rigid sheet by the temporary adhesive.

6. A method as in claim 1, in which the substrate is formed at least partially transparent to electromagnetic radiation used to operate the optical viewer whereby to allow the user to view the sheet of masking material through the substrate.

7. A method as in claim 1, in which the backing layer is demounted from the mount by a peeling step.

8. A method as in claim 1, in which the sheet of masking material provided comprises a material having a surface property adapted to allow only weak adherence of paint thereto.

9. A method as in claim 8 in which the said surface property comprises high surface energy.

10. A method of manufacturing a sensing element including carrying out the method of claim 1 and thereafter carrying out the steps of coating the sensing element having the series of masking elements applied thereto with a layer of corrosion-resistant material and thereafter removing the series of masking elements whereby to expose selected areas of the conducting tracks to corrosive influence.

11. A method as in claim 10, including the step of connecting the conducting tracks to a connection module adapted to allow connection of the conducting tracks of the sensor to monitoring means.

* * * * *